US 6,576,462 B2

(12) United States Patent
Thompson

(10) Patent No.: US 6,576,462 B2
(45) Date of Patent: Jun. 10, 2003

(54) VERMICULTURE COMPOSTING DEVICE

(76) Inventor: J. Michael Thompson, 721 Dorado Dr., Santa Barbara, CA (US) 93111

( * ) Notice: Subject to any disclaimer, the term of this patent is extended or adjusted under 35 U.S.C. 154(b) by 54 days.

(21) Appl. No.: 09/783,861

(22) Filed: Feb. 16, 2001

(65) Prior Publication Data

US 2002/0115199 A1 Aug. 22, 2002

(51) Int. Cl.[7] ................................................. C05F 9/02
(52) U.S. Cl. ............................... 435/290.1; 435/290.4; 435/810
(58) Field of Search ........................... 435/290.1, 290.4, 435/810; 71/8–10

(56) References Cited

U.S. PATENT DOCUMENTS 4,285,719 A * 8/1981 Criss ........................ 210/602

FOREIGN PATENT DOCUMENTS

| CH | 589014 A | * | 6/1977 | ........... C05F/09/02 |
|---|---|---|---|---|
| DE | 29712970 U1 | * | 9/1997 | ........... C05F/09/02 |
| EP | 1041059 A2 | * | 10/2000 | ........... C05F/09/04 |
| FR | 2507294 A | * | 12/1982 | ........... C05F/09/04 |
| WO | WO 9204303 A1 | * | 3/1992 | ........... C05F/17/02 |
| WO | WO 9962844 A1 | * | 12/1999 | ........... C05F/17/02 |

* cited by examiner

*Primary Examiner*—William H. Beisner
(74) *Attorney, Agent, or Firm*—Michael G. Petit

(57) ABSTRACT

The present invention relates to a composting device for composting organic waste, specifically animal and vegetable household waste. The device consists of a container having four rectangular sides, a base and a removable, reversible cover. The container is provided with a sealable compost extraction opening disposed on a front side of the container near the base. Ventilation openings are provided in the sides. One surface of the cover and front side of the container is painted dark to absorb sunlight and heat the interior chamber defined by the container. The opposing side of the cover is painted white to substantially reflect sunlight. The cover is removed and waste is added to the container through the top. Worms and microorganisms provide a way for degrading the waste into compost, which is removed through the extraction opening adjacent to the base for recycling. The temperature in the compost may be adjusted by increasing or decreasing absorption of sunlight. The temperature gradient thus formed in the container draws air through the ventilation openings and into the container to provide ventilation for the composting waste. In one embodiment, the composting device is provided in the form of a kit for home assembly.

8 Claims, 2 Drawing Sheets

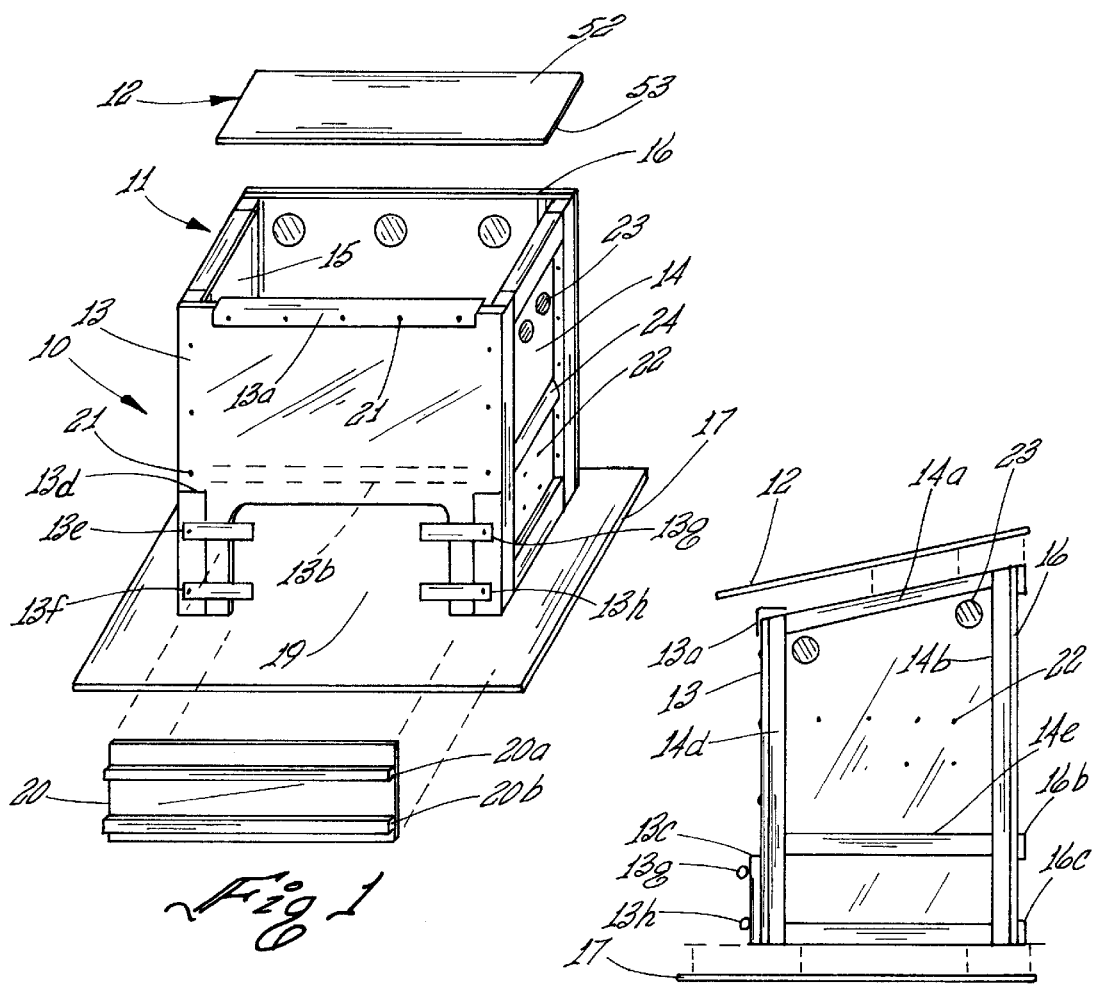
Fig 1
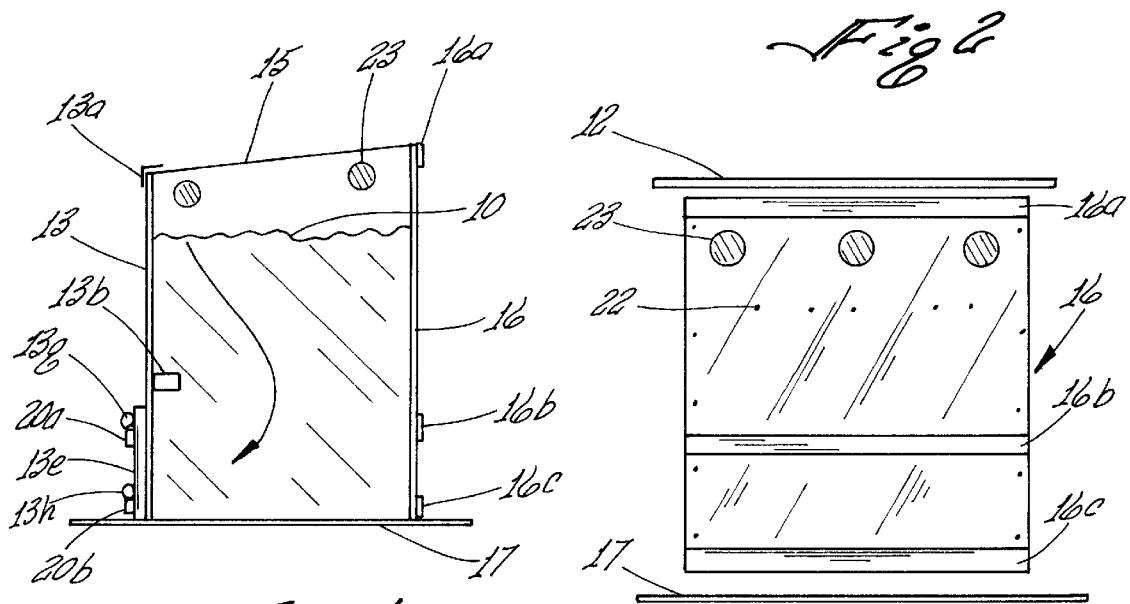
Fig 2
Fig 4
Fig 3

VERMICULTURE COMPOSTING DEVICE

BACKGROUND OF THE INVENTION

1. Field of the Invention

A composting device for the biodegradation and recycling of household waste and, more particularly, organic kitchen waste.

2. Prior Art

Organic waste recycling methods in which organic waste such as kitchen waste and newspaper are deposited into a composting container are well known in the art. Composting devices normally provide interim storage for such waste and provide and maintain environmental factors, including moisture, air, warmth and certain bacteria and worms (such as *Eisenia foetida, Eisenia hortensis* or *Eudrilus eugeniae*) and other wormlike organisms. The organic material is composted or digested to produce a pleasant smelling, uniform, well granulated compost that can be recycled as a plant food. Such devices are, in essence, bioreactors, wherein waste feed stock is converted into a desired product (compost) which may be inexpensively removed from the bioreactor for distribution, most preferably in a continuous process.

Numerous composting devices have been patented and are disclosed, for example, in U.S. Pat. No. 5,185,261 to Warrington, U.S. Pat. No. 5,413,934 to Fischer, U.S. Pat. No. 5,285,534 to Criss, U.S. Pat. No. 5,741,344 to Warkentin and U.S. Pat. No. 6,103,124 to Inoue. However only a few claim the ability to process ALL kitchen wastes. Unfortunately, these earlier art devices possess inherent deficiencies which have prevented them from becoming popular with consumers. There is a continuing need for a composting device that is inexpensive, easy to operate and adapted for home use.

SUMMARY

It is a first object of the invention to provide a device operable for converting organic kitchen waste into compost.

It is another object of the present invention to provide means for receiving organic kitchen waste and maintaining an environment suitable for the biodegradation of the organic kitchen waste.

It is still another object of the invention to provide a composting device that meets the foregoing objectives and which is adapted to be operable in a range of climatic conditions.

It is a further object of the invention to provide a composting device meeting the above objectives that can be sold in kit form and assembled by the end user.

The present invention discloses an earthworm or vermiculture based device for composting organic kitchen wastes, specifically fruits, vegetables, meat, fish, dairy, fats, oils, and bones. The device consists of a container having six rectangular parts: two sides, a top, a front, a back, a removable reversible cover, and an optional base. The container is provided with a sealable compost extraction opening which is disposed on the front panel of the container at its inferior surface. Variably dimensioned ventilation openings in the sides, front, and back provide for aeration of the bin. The front part or panel and one surface of the cover of the container is painted with a dark sunlight-absorbing color in order to solar heat the interior chamber defined by the container. The opposing side of the cover is painted white in order to substantially reflect sunlight, hence preventing chamber overheating during the warmer seasons or in tropical climates.

To operate the device, the consumer adds kitchen waste to the container through the top. A layer of soil, or bedding material such as shredded newspaper, or compost from the extraction opening, is placed over the waste. The worms, *Eisenia fetida, Eisenia hortensis, Eudrilus eugeniae* or other appropriate species act upon the waste in concert with aerobic microorganisms to convert the waste to compost. The finished compost may be periodically removed from the extraction opening and dispersed around the yard to recycle the nutrients.

The chamber temperature may be regulated by reversing the cover, and/or by orienting the front to face South in northern geographic locations, or to face North in areas in the southern hemisphere. In colder climates, or where sunlight is unavailable, insulation may be added to the exterior of the bin, and heating cables or heating mat may be attached to the inside of the container in order to maintain optimum chamber temperature. The thermal gradient thus formed by solar or other heat source draws oxygenating air in through the inferior ventilation openings, up through the bedding and wastes, and thence carries out through the superior ventilaton openings carbon dioxide and excess water vapor produced during the composting process.

A kit for home assembly is provided in one form of the embodiment. Detailed plans provide the do-it-yourself individual information for construction in another embodiment. Both embodiments would include seed populations of appropriate worm species as well as microbe inoculants.

The features of the invention believed to be novel are set forth with particularity in the appended claims. However the invention itself, both as to organization and method of operation, together with further objects and advantages thereof may best be understood by reference to the following description taken in conjunction with the accompanying drawings in which:

BRIEF DESCRIPTION OF THE DRAWINGS

FIG. 1 is a top perspective view of a vermiculture composting device in accordance with the present invention with the cover open.

FIG. 2 is a side elevational view of a vermiculture composting device in accordance with the present invention.

FIG. 3 is a rear perspective view of a vermiculture composting device in accordance with the present invention.

FIG. 4 is a side elevational view of a vermiculture composting device in accordance with the present invention with the side panel removed to show the flow pattern of the contents of the device.

DESCRIPTION OF THE PREFERRED EMBODIMENTS

Figure 5:
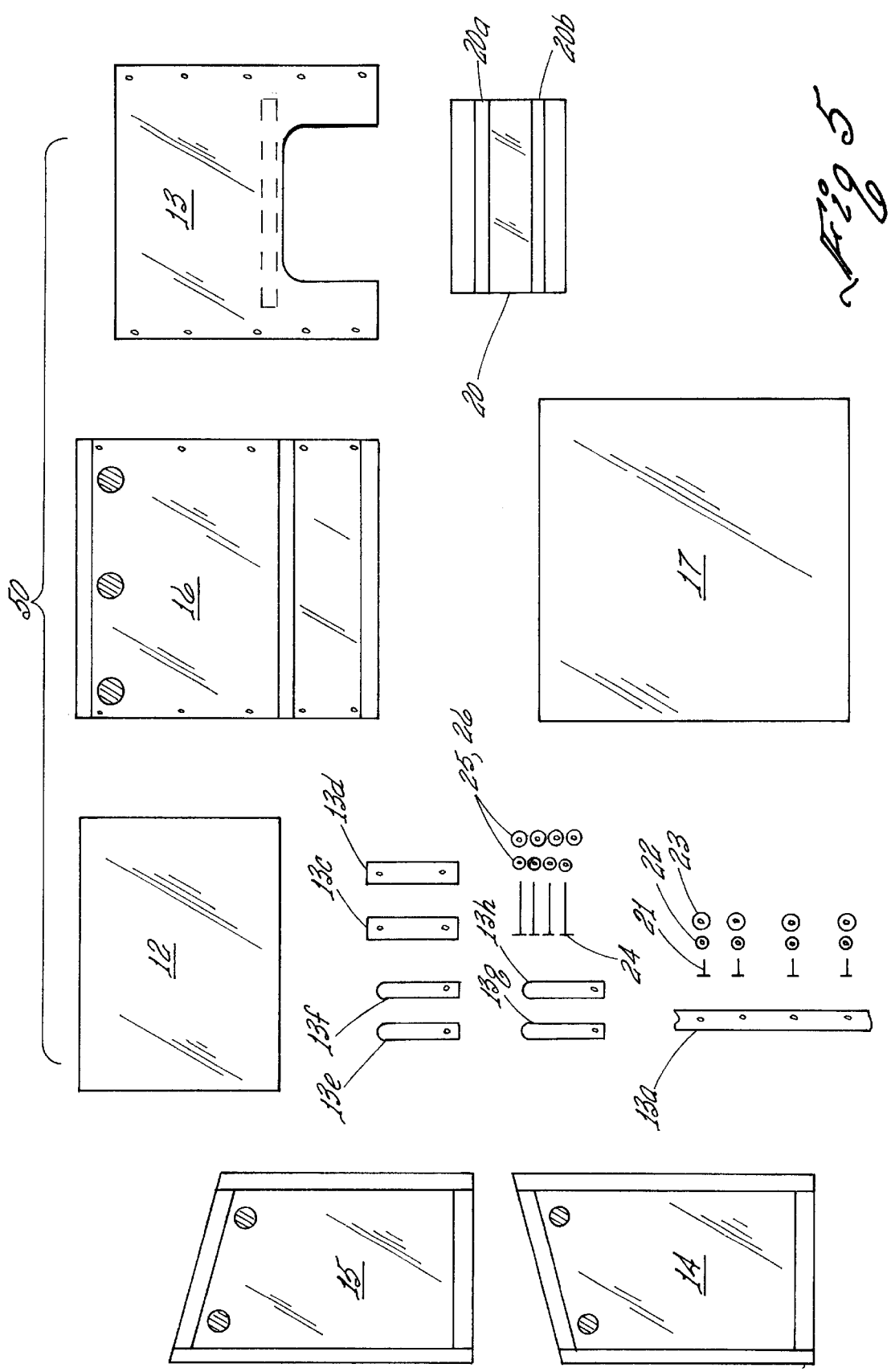
FIG. 5 is a plan view showing the unassembled components of the device.

A composting device 10 in accordance with the present invention is shown in top, front perspective view in FIG. 1. The composting device 10 includes a rectangular container 11 having a a removable cover 12, a front panel 13, with a removable extraction door 20, a right side panel 14, a left side panel 15, a rear panel 16, and an optional base 17. The panels comprising the device are preferably 0.5 inch thick five ply AB Exterior grade plywood or equivalently robust composite. The removable cover 12 measures approximately thirty three inches by twenty three inches. This cover 12 is epoxy resin sealed and is painted with a dark colored paint on one surface and a light or white paint on the other.

The front panel 13 measures approximately thirty inches high by thirty two inches wide and is epoxy resin sealed and painted a dark color on its exterior surface. This front panel 13 includes a galvanized steel angle iron 13a attached to its superior, uppermost edge with galvanized steel bolts 21. The front panel 13 inscorporates an extraction opening 19, which is sealed by a removable door 20. The door 20 has two reinforcing stringers 20a and 20b which also act as handles for removing the door 20, as well as stops for the pivoting locking bars 13e, 13f, 13g, and 13h. The front panel 13 also includes a two inch by two inch reinforcing stringer 13b secured to its inside surface above the extraction opening 19. In addition, two spacers 13c and 13d provide anchorage for the locking bars 13e, 13f, 13g, and 13h, and also provide said locking bars sufficient clearance from the front panel 13 in order that they may pivot about their anchor points. The door 20 may be independent or hinge-attached to the front panel 13. A number of ventilation orifices 22 are spaced over this panel's surface. The front panel 13 is assembled with the side panels 14 and 15 and held in place with hot dipped galvanized steel bolts 24, washers 25, and nuts 26.

The right side panel 14 measures approximately thirty inches high on its front edge, thirty three inches high on its rear edge, and twenty two inches wide. It is epoxy resin-sealed and painted a variable color on its exterior surface. Five two inch by two inch wood stringers 14a, 14b, 14c, 14d, and 14e are glued and nailed to its periphery and to a point approximately ten inches superiorly from its inferior (lowest) edge. There are a number of variably dimensioned apertures 22 and 23 disposed in the side panels of the bin 10 for ventilation. The left side panel 15 measures approximately thirty three inches high on its rear edge, thirty inches on its front edge, and twenty two inches wide. The panel 15 is sealed with epoxy resin and painted a variable color on its exterior surface. Five two inch by two inch wood stringers 15a, 15b, 15c, 15d, and 15e are glued and nailed to its periphery and to a point approximately ten inches superiorly from its inferior edge. A number of variably dimensioned apertures 22 and 23 perforate its surface.

The rear panel 16 measures approximately thirty three inches high by twenty two inches wide. It is epoxy resin-sealed and painted with a variably colored exterior grade paint on its exterior surface. Reinforcing wood stringers 16a, 16b, and 16c are glued and nailed to its superior three inches, bottom edge, and approximately ten inches up from the bottom edge respectively. A number of variably dimensioned ventilation orifices 22 & 23 penetrate the rear panel 16. The base panel 17 measures approximately thirty two inches wide by forty four inches deep. It is epoxy resin-sealed and painted with a variably colored exterior paint on its superior surface. There are no ventilation apertures 22 or 23 in the base panel 17.

With reference to FIG. 5, a kit in accordance with the present invention is illustrated in plan view. The dimensions of the optional base 17 may vary considerably but is preferably about 32 inches long, 44 inches wide and 0.5 inches thick. The side panels 14 and 15 are preferably about 30 and 33 inches high, 22 inches wide and 0.5 inches thick. The front panel 13 is about 32 inches wide and 30 inches high and the rear panels 16 is preferably about 33 inches high and 32 inches wide. The removable cover 12 is dimensioned to cover the assembled container. Four bolts 21, together with four nuts 22 and washers 23 are preferably used to rotatably attach the locking bars 13e–h to the front panel 13. The extraction opening is preferably about 15 inches long and 10 inches deep with the door 20 dimensioned accordingly.

An important aspect of the present invention is the use of solar energy to regulate temperature within the container and to generally maintain the environmental variables in a range suitable for biodegradation of the waste. The sealing engagement of the door 20 and cover 12 with the container 11 retains moisture within the container. The cover 12 has a top surface 52 and a bottom surface 53. The top surface 52 is coated with a layer of non-reflective paint (not shown) and the bottom surface 53 is coated with a layer of reflective paint (not shown). Since the cover 12 is reversible, when the external temperature is low and the temperature within the container drops below optimal, the non-reflective surface of the container is disposed to absorb solar energy to heat the container. Conversely, when the temperature within the container rises above optimal, the cover is reversed to place the reflective surface thereof to receive solar energy, thereby reducing or preventing further heating of the container by solar energy. The kit 50 may further include weather resistant nails or screws 24 and associated bolts 24 and nuts 25 and/or washers 26.

The present invention affords the user numerous advantages over existing devices in its class. My compost bin exhibits simplicity in form; the device being a free-standing box open at both ends. This device can be easily constructed with simple hand tools from readily available materials. Because this compost bin is constructed of plywood and is epoxy resin stabilized, it is strong, light, and will never rot. My compost bin provides the user convenience and reliability because of what it lacks: there are no motors, valves, pumps, or screens that clog. The device has only four moving parts. The bin's "upkeep" consists of merely applying a fresh coat of paint once or twice each decade. In addition, positioning the assembled compost bin is facile. The plywood base can be set upon most any substrate including bare ground or turf. If a concrete slab or similar surface is available, the present device's optional base can be excluded. The present device' small footprint permits its placement more easily where space is limited.

Recycling all kitchen wastes from start to finish goes quickly and easily. There is no need to separate different classes of waste, simply scrape one's plate leftovers (including paper napkin) into an approximately one gallon plastic container that has been lined with a cellulose napkin or paper towel and is normally kept next to the sink. At day's end this plastic container of accumulated kitchen waste is emptied into a five-gallon plastic pail with lid. This pail is lined with one or two sheets of newspaper to facilitate cleaning and stored outside. Once each week (the average over time for a family of four), the five-gallon pail is emptied into the top of the compost bin. Approximately two and one-half gallons, or a half-bucket, of garden soil is then spread over the top of the waste in the bin. An equivalent amount of shredded newspaper bedding, or compost taken from the extraction opening of the bin may be used in place of garden soil to cover the waste. Covering the wastes allows the microbes and worms access from all sides and prevents flies from entering or odors from developing.

Clean-up consists of putting the one gallon kitchen-based container in the dishwasher nightly and garden-hose-spraying the five gallon bucket weekly. This entire process takes less time than is required for adding compostable material to prior art devices. I believe this process/device to be more time-efficient than putting kitchen wastes down the sink macerator (and certainly more conservative of precious potable water inasmuch as each pound of kitchen waste macerated requires co-disposal of seven gallons of fresh water.) The device and process of the present invention is cost-effective when compared to the financial burdens of expanding and operating wastewater treatment plants or land fills. Finished compost can easily be periodically shoveled from the large extraction opening and used to replenish/enhance soil fertility in the local landscape.

This device allows continuous composting of kitchen wastes as the result of a unique modified vertical flow of the chamber contents: the reinforcing stringer attached to the inside of the front panel acts as a baffle. This baffle diverts the flow of composting waste and bedding from a straight vertical flow to a 'J' curve flow. This unique flow allows more complete waste composting while maintaining a compact vertical dimension for the device. Thus the present compost bin operates with a continuous flow pattern to produce a nutrient-rich soil product in a short period and without odors or fuss. Because of the novel proportions of my device, the worms may migrate within the chamber to microclimate regions where conditions are optimum for their physiology. For example, if waste such as a liquid vegetable oil marinade is added in significant volume (one or two quarts) this oil would normally smother earth worms. In devices with smaller volumes, the worms would have no place to escape. The worms prefer an oil substrate. With my device, the worms can move vertically a sufficient distance to safety, then feed upon the oil from the periphery.

My device demonstrates 'thermal advantages' over prior art devices. During hot periods of the day, the bedding/compost/wastes may overheat in other devices exposed to direct sunlight. This overheating may occur despite ventilation openings (which I believe my invention utilizes more efficiently due to its unique ability to develop a 'stack effect' updraft). With my device, should overheating occur, the worms can migrate vertically and/or horizontally to cooler microclimate regions within the bin chamber. The vermiculture composting bin has been designed with attention to small details that ensure convenience and durability. The galvanized steel angle iron at the top of the front panel serves the dual role as panel reinforcement and shield. When the user is shoveling soil and/or compost, some soil or compost frequently adheres to the shovel blade. The angle iron provides a convenient device upon which to tap the shovel in order to remove adherent materials.

The present compost bin has been engineered to be 'bullet resistant'. It may operate efficiently for generations. My prototype device has functioned well for more than two decades. My vermicomposting bin has successfully recycled all of the kitchen waste produced by my family of four, as well as the periodic "shock loads" associated with holiday parties and fishing adventures. I believe that this device and its process have achieved a mastery of the science of kitchen waste recycling.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A vermiculture composting device comprising:
   (a) a rectangular container having two sides, a rear panel and a front panel;
   (b) a rectangular extraction opening in said front panel;
   (c) a removable, rectangular cover having a reflective surface and a non-reflective surface reversibly attached to an upper edge of said two sides, said rear panel and said front panel, said rectangular cover being operable for absorbing sunlight and heating said device when the ambient temperature is below an optimum temperature for vermiculture and for reducing heating of the device by reflecting sunlight when the ambient temperature is greater than the optimum temperature for vermiculture;
   (d) a door adapted to engage said front panel, said door thereafter sealing said extraction opening in said front panel; and
   (e) locking means attached to said container, said locking means being operable for holding said door in sealing engagement with said front panel.

2. The vermiculture composting device in accordance with claim 1 further comprising a base dimensioned to support said rectangular container.

3. A kit for constructing a composting device comprising:
   (a) two first rectangular sheets of a building material, said sheets being operable for forming left and right sides of a container;
   (b) two second rectangular sheets of building material wherein one of said second rectangular sheets is a front panel having an extraction opening therein, and a rear panel wherein said two second rectangular sheets are adapted to join together said two first rectangular sheets to form a container having walls defining a rectangular interior chamber;
   (c) a door dimensioned to seal said extraction opening; and
   (d) a cover having a reflective surface and a non-reflective surface, said cover being adapted to be reversibly attached to a top of said container, said cover being operable for absorbing sunlight and heating said container when the ambient temperature is below an optimum temperature for vermiculture and for reducing heating of the container by reflecting sunlight when the ambient temperature is greater than the optimum temperature for vermiculture.

4. The kit of claim 3 further comprising a third rectangular sheet of building material adapted to form a base for said container.

5. The kit of claim 4 further including handles for said door.

6. The kit of claim 5 further including a locking bar adapted for rotatable attachment to said container.

7. The kit of claim 3 further comprising worms of a species adapted for survival when exposed to climatic conditions corresponding to a particular geographic area.

8. The kit of claim 7 further comprising an inoculum of microorganisms operable for biodegrading organic waste material.

* * * * *